United States Patent [19]

Dauer et al.

[11] Patent Number: 5,510,517
[45] Date of Patent: Apr. 23, 1996

[54] PROCESS FOR PRODUCING N-AMINO-1-HYDROXY-ALKYLIDENE-1,1-BISPHOSPHONIC ACIDS

[75] Inventors: Richard R. Dauer, Longmont, Colo.; Lisa DiMichele, North Plainfield, N.J.; Mauricio Futran; Gerard R. Kieczykowski, both of Westfield, N.J.

[73] Assignee: Merck & Co., Inc., Rahway, N.J.

[21] Appl. No.: 286,151

[22] Filed: Aug. 4, 1994

Related U.S. Application Data

[63] Continuation-in-part of Ser. No. 239,640, May 9, 1994, abandoned, which is a continuation of Ser. No. 111,751, Aug. 25, 1993, abandoned.

[51] Int. Cl.$^6$ .................................................... C07F 9/28
[52] U.S. Cl. .................................................... 562/13
[58] Field of Search .................................................... 562/13

[56] References Cited

U.S. PATENT DOCUMENTS 5,019,651   5/1991   Kieczykowski ........................... 562/13

Primary Examiner—José G. Dees
Assistant Examiner—Joseph M. Conrad, III
Attorney, Agent, or Firm—Joanne M. Giesser; Melvin Winokur

[57] ABSTRACT

A process for continuously producing alkylpyrophosphonate, alkylpyrophosphate and multimers thereof and for producing 4-amino-1-hydroxyalkylidene-1,1-bisphosphonic acids or salts thereof.

5 Claims, No Drawings

PROCESS FOR PRODUCING N-AMINO-1-HYDROXY-ALKYLIDENE-1,1-BISPHOSPHONIC ACIDS

BACKGROUND OF THE INVENTION

This application is a continuation-in-part of U.S. patent application Ser. No. 08/239,640, filed May 9, 1994 now abandoned, which is a continuation of U.S. patent application Ser. No. 08/111,751, filed Aug. 25, 1993, now abandoned.

This invention relates to a process for continuously producing alkylpyrophosphonates, alkylpyrophosphates and multimers thereof and in particular for producing 4-amino-1-hydroxybutylidene-1,1-bisphosphonic acid and salts thereof, where the end product is obtained in particularly pure form and at high yields in a continuous reaction.

It is known according to U.S. Pat. No. 4,407,761 to Henkel Kommanditgesellschaft to prepare 4-amino-1-hydroxybutylidene-1,1-bisphosphonic acid with phosphonating reactants and then quenching the reaction mixture by the addition of a strong non-oxidizing agent, preferably concentrated hydrochloric acid, with heating, to hydrolyze the formed phosphorous intermediates to final product. However, this phosphonation reaction does not remain homogeneous, thereby producing heterogeneous solidification of the reaction mixture. This solidification causes variable yields and leads to the development of "hot spots" which in part result from the exothermic nature of the reaction. Moreover, to make the sodium salt, using the prior art processes, requires isolation of 4-amino-1-hydroxybutylidene-1,1-bisphosphonic acid and an additional step to convert this to the monosodium salt. Further, the use of concentrated hydrochloric acid in the quench, whose fumes present an environmental problem, is also required.

U.S. Pat. No. 4,922,007 to G. R. Kieczykowski, et al., (assigned to Merck & Co., Inc.) discloses the use of methanesulfonic acid to overcome the non-homogeneity and solidification problems associated with the formation of intermediates during the bisphosphonation phase. However, this process utilizes a non-pH controlled water quench that leads to the presence of a strongly acidic and corrosive hydrolysis mixture which requires specialized equipment.

U.S. Pat. No. 5,019,651 to G. R. Kieczykowski, et al., (assigned to Merck & Co., Inc.), discloses using a pH controlled quench step in the range of 4 to 10, followed by hydrolysis, that eliminates the concentrated hydrochloric acid formed in the quench step and the need to handle a corrosive acidic product hydrolysis mixture.

Prior methods teach the requirement that the reaction be completed at temperatures above the boiling point of $PCl_3$, for instance 90° C. However, this temperature is known to be in the adiabatic self-heat range that is an unsafe operating range as batch volumes increase and available cooling capacity decreases. In addition, control of stoichiometric ratio is important to achieving useful intermediates. However, control of stoichiometric ratios at constant temperature, typically 90° C., is impossible using prior batch methods because stoichiometric quantities of $PCl_3$ may only be added at sub reflux temperatures. For example, in U.S. Pat. No. 5,019,651, stoichiometric ratios were achieved by use of temperature programming whereby the stoichiometric amount of $PCl_3$ could be added at sub-reflux temperatures. Alternatively, in U.S. Pat. No. 4,407,761, $PCl_3$ was added slowly at isothermal reaction temperatures above $PCl_3$'s boiling point. Thus, it is desirable to control both stoichiometry and reaction temperature at the same time to provide consistent distribution of useful intermediates and to ensure a safe operating environment. The prior batch modes of operation made control of stoichiometric ratios impossible while maintaining a constant temperature.

The present invention solves both of these problems through operation of the reaction in a continuous stirred tank reactor that allows greater heat transfer for temperature control while maintaining constant stoichiometric ratios of reactants. The more favorable surface to volume ratio of the present invention allows greater heat transfer for temperature control. Further, continuous steady operation results in fixed ratios of products and intermediates in a small controllable environment by controlling both reaction temperature and stoichiometric ratio at all times. The smaller reacting mixture reduces severity of an unexpected thermal event and allows the entire reacting mixture to be quenched.

SUMMARY OF THE INVENTION

By this invention, there is provided a process for the continuous preparation of compounds of the structural Formula I $$Z\text{—}R_1$$

I wherein Z is selected from the group consisting of:

a) $H_2N\text{—}C_{2-5}alkyl\text{—}$;

b)

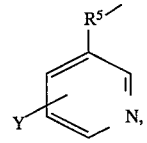

wherein $R^5$— is $C_{1-5}alkyl$, and Y is selected from (i) hydrogen;

(ii) $C_{1-5}alkyl$;

(iii) $R^6O$;

(iv) $R^6S$;

(v) $R^6R^6N$;

(vi) halogen;

$R^6$ is H or $C_{1-5}alkyl$; and c) $C_{2-6}alkylI\text{—}(N\text{—}CH_3)C_2H_4\text{—}$; and $R_1$ is a member selected from the group consisting of:

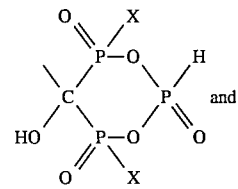 a)

and

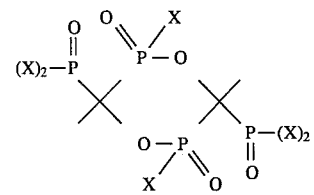 b)

wherein X is OH or Cl. This invention also provides a process for the continuous production of intermediate compounds of Formula IIA, IIB and IIC

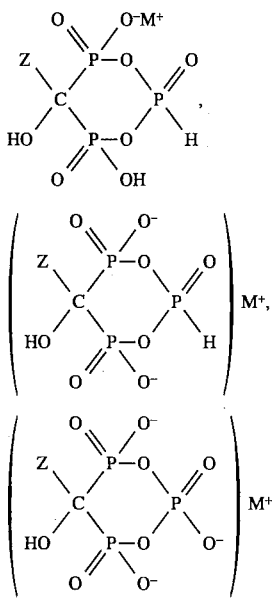

wherein Z is defined as above, and M is a monovalent, divalent or trivalent cation such as $Na^+$, $K^+$, $Ca^{2+}$, $Mg^{2+}$. It should be noted that all ionic forms of these intermediate compounds are encompassed by this invention. This invention further includes a process for the continuous production of compounds of Formula IIIA, IIIB, and IIIC

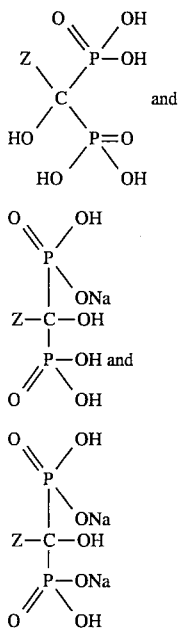

that comprises:

a) continuously mixing an aminoalkane carboxyiic acid of formula

Z—COOH, wherein Z is as defined previously, with $H_3PO_3$ and $PCl_3$ in methanesulfonic acid (MSA), or optionally $PCl_3$ in MSA; and b) continuously adding aqueous base to the overflow mixture containing the compound of Formula I to produce the compounds of Formula II; and c) hydrolyzing the overflow mixture containing the compounds of Formula II to produce the compounds of Formula III; and d) recovery of the products of Formula III and salts thereof.

It is noted that all possible hydrated forms are contemplated by this invention. For compounds of Formula IIIB, a trihydrate is a preferred embodiment.

In a preferred embodiment, the compound is of the Formula Ia, Z—$R_1$ wherein Z is group a) $H_2N$—$C_{2-5}$alkyl. Preferred intermediate compounds of the Formula IIa include compounds of the Formulas IIa(i) and IIa(ii):

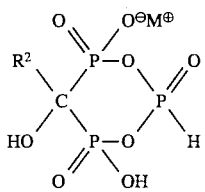

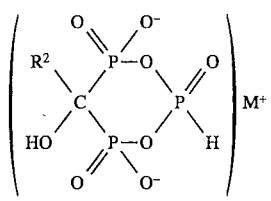

wherein $R^2$ is $C_{2-5}$alkyl substituted with a terminal amine or a protonated terminal amine.

This invention preferably includes a process for the continuous production of compounds of the Formula IIIa(i), IIIa(ii), and IIIa(iii).

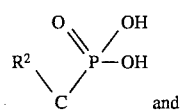

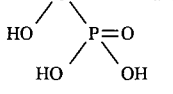

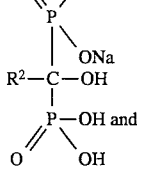

wherein $R^2$ is $C_{2-5}$alkyl substituted with a terminal amine, and the compounds may be in any hydrated state or a protonated terminal amine, said process comprising:

a) continuously mixing an aminoalkane carboxylic acid of the formula

$H_2N$—$C_{2-5}$alkyl—COOH with $H_3PO_3$ and $PCl_3$ in methanesulfonic acid (MSA), or optionally $PCl_3$ in MSA; and b) continuously adding aqueous base to the overflow mixture containing the compound of Formula Ia to produce the compounds of Formula IIa; and c) hydrolyzing the overflow mixture containing the compounds of Formula IIa to produce the compounds of Formula IIIa: and d) recovery of the products of Formula IIIa and salts thereof.

DETAILED DESCRIPTION OF THE INVENTION

This invention relates to compounds of the structural Formula I

Z—R₁

I wherein Z is selected from the group consisting of:
a) $H_2N-C_{2-5}alkyl-$;
b)

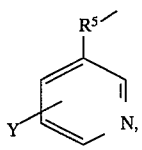

wherein $R^5-$ is $C_{1-5}$alkyl, and Y is selected from
(i) hydrogen
(ii) $C_{1-5}$alkyl;
(iii) $R^6O$;
(iv) $R^6S$;
(v) $R^6R^6N$;
(vi) halogen;
$R^6$ is H or $C_{1-5}$alkyl; and c) $C_{2-6}alkyl-(N-CH_3)C_2H_4-$; and
wherein $R_1$ is a member selected from the group consisting of:

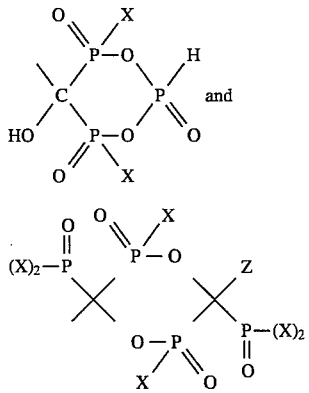

wherein X is ⁻OH or ⁻Cl. The present invention is also directed to a process for producing said compounds and the bisphosphonate products thereof including 4-amino-1-hydroxybutylidene-1,1-bisphosphonic acid (ABP) and salts thereof. Specifically, this process may consist of five operations: continuous bisphosphonation reaction, continuous or batch pH controlled quench, continuous or batch hydrolysis, crude crystallization, and pure crystallization.

More specifically, the continuous bisphosphonation reaction consists of producing an carboxylic acid feed and reacting this feed with $PCl_3$ in a continuous stirred tank reactor.

The carboxylic acid feed is assembled by dissolving solid carboxylic acid and solid phosphorous acid ($H_3PO_3$) in methanesulfonic acid (MSA). Generally, 1 to 3, preferably 2 moles of $H_3PO_3$ and generally 6.3 to 6.4, preferably about 6.38 moles of MSA are used per mole of carboxylic acid. To facilitate complete dissolution of the solid components in the liquid MSA, the mixture can be heated from 40° C. to 90° C., preferably 70° C. Once the solid components of the carboxylic acid feed are dissolved, this feed may be maintained from 10° C. to 90° C., preferably 70° C. using an external heat source. Alternately, the $H_3PO_3$ addition may be eliminated in the carboxylic acid feed preparation. If this alternate procedure is chosen, then $H_3PO_3$ may be formed in situ from $PCl_3$ in methanesulfonic acid (MSA), $PCl_3$ and γ-amino butyric acid (GABA) in MSA, or $H_2O$ in MSA.

The carboxylic acid feed is added to the cold reaction vessel to a point below the overflow level. During this fill, a heating medium is placed in the jacket and the vessel agitator tuned on. Temperature control is used to bring the temperature up to about 45°–100° C., preferably 90° C. The liquid $PCl_3$ feed is then initiated to the reactor vessel until the weight of $PCl_3$ fed to the reactor (adjusted for vapor loss) divided by the weight of carboxylic acid feed is from 0.22–0.33, preferably 0.32. At this point, the carboxylic acid feed is resumed at a flowrate sufficient to provide a residence time in the reactor from about 1.5–2.5 hours, preferably 1.8 hours. The residence time is expressed as the volume of the reactor overflow conditions divided by the flowrate (vol/min) of carboxylic acid feed. Shortly after the carboxylic acid feed is resumed, the reactor will overflow into the quench vessel which can initially be filled with either water or dilute aqueous base. The carboxylic acid and liquid $PCl_3$ are added simultaneously at their respective flowrates until the desired amount of material is produced.

Three residence times for the bisphosphonation reaction are undertaken before steady state synthesis occurs. Prior batch processes result in the uncontrollable formation of unwanted intermediates. The present invention overcomes this problem through stoichiometrically controlling the reaction components thereby minimizing the formation of unwanted intermediates.

The overflowing batch is neutralized in an attached quench vessel by the addition of aqueous base. The aqueous base may be any aqueous base of the formula MOH such as sodium hydroxide, or of the formula $MHCO_2$ or $MCO_2$ such as sodium carbonate or sodium bicarbonate, wherein M is any ion. Separate deionized (DI) water and base feeds are utilized to maintain an effective concentration of base in the quench solution from about 15–50%, preferably about 20%. Aqueous base is added to maintain pH in response to fluctuations in the pH of the quench solution. The pH in the quench vessel is maintained between 4.0 and 7.0, preferably about 5.0. The temperature of the quench mixture may be maintained from 0° C. to 100° C., preferably <50° C.

The bisphosphonation mixture produces compound of Formula I.

Z—R₁

I wherein Z is selected from the group consisting of:
a) $H_2N-C_{2-5}alkyl-$;

b)

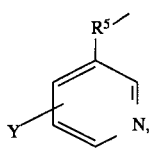

wherein R⁵— is $C_{1-5}$alkyl, and Y is selected from
(i) hydrogen;
(ii) $C_{1-5}$alkyl;
(iii) R⁶O;
(iv) R⁶S;
(v) R⁶R⁶N;
(vi) halogen;
R⁶ is H or $C_{1-5}$alkyl; and c) $C_{2-6}$alkyl—(N—CH₃)C₂H₄—; and
wherein R₁ is a member selected from the group consisting of:

a) 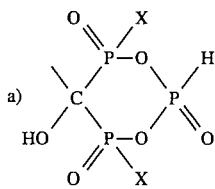

and b) 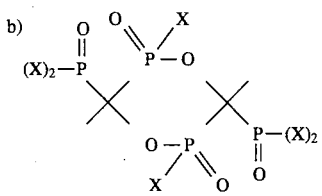

wherein X is ⁻OH or Cl. It is likely that the compound of the following formula

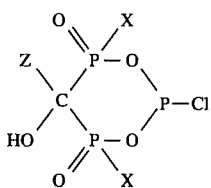

is also formed prior to quenching. Preferred compounds according to this invention are as follows. For compounds of the formula Z—R₁, where Z is a) H₂N—$C_{2-5}$alkyl—, Z is preferably a H₂N—C₄alkyl and the resulting compound may be used as an intermediate for the production of alendronate (4-amino-1-hydroxybutylidene-1,1-bisphosphonic acid, sodium salt trihydrate.)

For compounds where Z=b), the preferred compound is where R⁵ is CH₂, and the resulting compound may be used as an intermediate for the production of risedronate (1-hydroxy-2-(3-pyridinyl)ethylidene bisphosphonic acid.

For compounds where Z=c) a preferred compound is where Z=C₄alkyl—(N—CH₃)C₂H₄—. This can be used as an intermediate for the production of the compound designated BM210955. (1-hydroxy-3-(methylpentylamino)propylidenebisphosphonate).

This reaction and/or the bisphosphonation mixture itself exhibits significant exothermic characteristics. Therefore sufficient safety precautions must be undertaken to assure the reaction proceeds safely. To this end, for a given productivity, the smaller reaction volume of the continuous reaction provides faster quench time in the event of reaction runaway than a batch system of similar productivity. The vessel that receives the normal overflow from the bisphosphonation reaction is also employed for the emergency quench. The minimum volume of the emergency quench is about twice the reaction volume of the reactor vessel. This enables the entire reaction volume to be quickly quenched in the event of an undesired thermal event.

The compound of Formula IIA, IIB; or IIC:

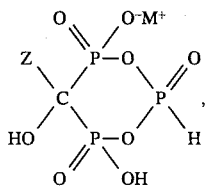 IIA

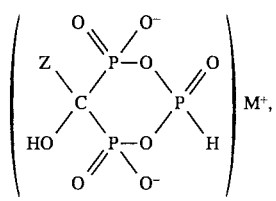 IIB

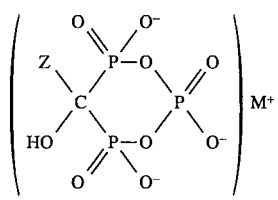 IIC wherein Z is as defined previously, and preferably a $C_{2-5}$ alkyl substituted with a terminal amine or a protonated terminal amine and M⁺ is a monovalent or a divalent cation such as Na+, K+, Ca²⁺, Mg²⁺, may be accumulated or may be continuously removed from the quenching vessel via overflow into a new reactor for hydrolysis. It should be appreciated that other anionic forms of compounds of Formula II, for example tri-ionic, are formed under appropriate pH conditions: (structures throughout this specification should be understood as including all possible ionic forms dependent on the pH of the environment). The pH of the quenched material is checked and adjusted, if necessary, to between about 3.3 to 12.3, preferably to about 4.6 and 5.0. The batch is heated in a vessel composed of thick walled PYREX™, or if vessel degradation is a problem, then in a vessel lined with Hastealloy™ C-276, to about 100°–175° C., preferably 140° C. at 60 psig and aged for about 20 hours to breakdown Compounds IIA and IIB into product III.

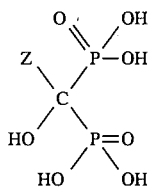 III wherein Z is as defined previously and is preferably a $C_{2-5}$ alkyl substituted with a terminal amine and salts thereof, particularly the monosodium and disodium salts.

The batch is then cooled to 85° C. and a sample is taken to confirm pH and completion of hydrolysis. However, hydrolysis of the pyrophosphonate may be carded out at room temperature and recovery of the desired end product is possible. The batch volume may be adjusted before or after the hydrolysis by either distillation or the addition of water. Pure mother liquors may be returned to the batch before hydrolysis and the excess volume taken off by distillation to ensure the total solids specification for the crude crystallization is met.

The pH of the warm solution is corrected if needed by the addition of an appropriate acid or base. After the pH adjustment at 85° C., the hydrolyzed batch may be seeded with crude or pure compound of Formula III or its mono or di- salt forms which may be present at the appropriate pH.

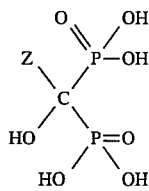   III

The batch is cooled to 0°–25° C. This crude solution is aged for >6 hours and the crystal slurry is isolated by filtration. The resulting cake may be washed with cold, deionized water. The crude cake may be dried or charged directly into the purification step.

The crude undried mixture and deionized water are added to the purification vessel. The vessel temperature is taken up to from about 40° C. to about 100° C., preferably 50° C. and the solution aged until dissolution is complete. The recovery of end product is pH dependent, from about pH 3.0 to about pH 12.0. Preferably, the pH is adjusted to 4.3 to obtain the mono salt. The batch is filtered and then concentrated by distillation. The resulting slurry is cooled to from about 0° C. to about 5° C. and aged for longer than two hours. The chilled slurry is filtered and the wetcake washed with cold deionized water (0°–5° C.) and then dried in vacuo. The compound of Formula III

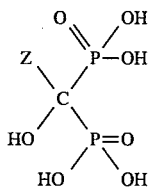   III wherein Z is as defined previously and is preferably a $C_{2-5}$ alkyl substituted with a terminal amine and salts thereof, particularly the monosodium and disodium salts, is obtained by this process.

The reaction is schematically represented as follows when the base is NaOH:

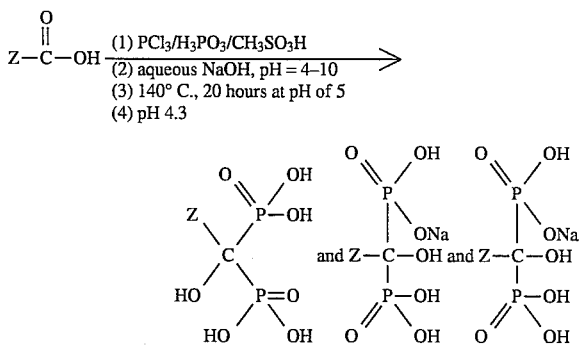

wherein Z is defined previously and is preferably a $C_{2-5}$ alkyl substituted with a terminal amine.

A particular illustration of this reaction wherein Z is $NH_2$—$CH_2$—$CH_2$—$CH_2$ leads to

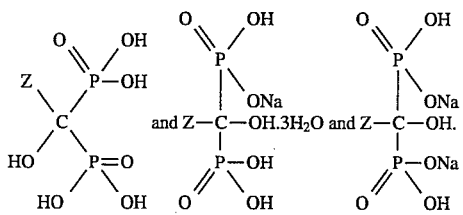

The bisphosphonic acids described here are useful because of their sequestering power for polyvalent metal ions and for complex formation with alkaline earth ions, preferably calcium ions. Therefore, substituted bisphosphonic acids may be useful in water softening, water purification, and in the preparation of non-toxic pharmaceutical medicaments.

Specifically, 4-amino-1-hydroxybutylidene-1,1-bisphosphonic acid monosodium salt trihydrate described here is useful as a pharmaceutical composition and for the treatment or prevention of diseases involving bone resorption. Such diseases as hypercalcemia of malignancy, Paget's disease and osteoporosis are advantageously treated with 4-amino-1-hydroxybutylidene-1,1-bisphosphonic acid monosodium salt trihydrate made according to the process of the present invention.

Other pharmaceutically acceptable salts, such as for example potassium salts, can be prepared according to the processes of the present invention and are included within the scope thereof. Other bisphosphonates that may be prepared by this continuous process include (a) 2-amino1-hydroxyisobutylidene-1,1-bisphosphonic acid, (b) 3-amino-1-hydroxypropylidene-1,1-bisphosphonic acid, (c) 5-amino-1-hydroxypentylidene-1,1-bisphosphonic acid (d) 6-amino-1-hydroxy-hexylidene-1,1-bisphosphonic acid, (e) risedronate, (1-hydroxy-2-(3-pyridinyl)ethylene-1,1-bisphosphonic acid, and (f) BM210955 N-butyl-N-methyl-3-amino-1-hydroxypropylidine-1,1-bisphosphonic acid.

The following examples are illustrative of the practice of the invention without being limited in any way.

EXAMPLE 1

Continuous preparation of 4-amino-1-hydroxybutylidene-1,1-bisphosphonic acid 2.6 kgs of MSA was charged to a reactor flask. 0.545 kg of GABA was charged into the flask with stirring followed by a charge of 0.865 kg $H_3PO_3$. This mixture of MSA, GABA and $H_3PO_3$ shall hereinafter be referred to as the GABA Feed. The mixture was maintained at 70° C. during dissolution. The remaining 0.645 kg of MSA was added as a rinse and the solution stirred at 70° C. until GABA and $H_3PO_3$ were dissolved.

The bisphosphonation reactor was jacketed and fitted with a mechanical agitator, feed ports, temperature probe, and a reflux-condenser and a bottom outlet. A standard hydrogenation mixing configuration was used to design the reactor. The reactor includes four half baffles set 90° C. apart extending from the bottom of the reactor. A Rushton turbine type agitator is located at the bottom of the impeller shaft. Also attached to the impeller shaft and located above the Rushton turbine was a propeller type agitator. The propeller type agitator had a larger diameter than the Rushton type turbine. The jacket surrounding the reactor was located beneath the wetted wall. The bath used to heat the jacket medium was set between 97°–105° C. depending on the heat load requirements of the reaction mass to maintain a batch temperature of 90° C. The condenser and medium were set to achieve an off-gas temperature of –10° C.

Before the continuous bisphosphonation reaction reached steady state a semi-batch start up was employed. The reactor bath was set to 97° C. to maintain temperature of reaction mass at 90° C. The reactor jacket was not circulated until the GABA feed was charged to the reactor. The bath temperature was continuously adjusted as needed to maintain batch temperature of 90° C. The $PCl_3$ reservoir was filled and refilled as needed. The GABA feed reservoir was filled and refilled as needed. The reactor vessel was filled with 400 ml of the warm GABA feed. At this time agitation and bath circulation of the reactor jacket commenced. The GABA feed in the reactor was heated to 90° C. 50 ml of GABA feed was drained from the reactor. $PCl_3$ flow was initiated into the reactor at 0.95 ml/min. After 95 minutes, the flow of the GABA feed was initiated at 3.7 ml/min. This time corresponds to 90 ml of $PCl_3$ entering the reactor and a ratio of $PCl_3$/GABA feed of 0.33 (g/g). At this stage, the semi-batch start-up procedure was completed and the continuous operation mode was established.

$PCl_3$ and GABA feeds were continued at 0.95 ml/min. and 3.7 ml/min., respectively, for the desired run time. The flowrates were chosen to give a residence time of 1.8 hours based on the flow rate of GABA feed. During the entire process, the reactor was overflowing into the quench vessel. The yield to intermediates that will subsequently be available after hydrolysis for recovery is about 60–72%, typically 70% at steady state. This is 10% above the yield expected from a direct change from batch to continuous mode.

The amount of material needed was the limiting factor in the length of the run. At the end of the run, the $PCl_3$ and GABA feeds were turned off. The reactor was drained once $PCl_3$ was no longer refluxing.

Continuous quenching took place in a 500 ml cylindrical, jacketed reaction flask with an attached overflow leg and a teflon paddle stirring mechanism. The pH probe for the quench was calibrated with buffer solutions of pH 4.0 and 7.0. The lower limit was set at 5.0. The 47% NaOH reservoir was filled and maintained. The deionized (DI) water or the pure mother liquor reservoir was filled and maintained. During the semi-batch start-up, the flow rate of the aqueous NaOH solution was calibrated to 12.3 ml/min. The DI water or the pure mother liquor reservoir flow rate was calibrated to 18.75 ml/min. An initial charge of 700 ml of DI water was placed in the quench vessel. As reaction mass from the bisphosphonation reaction reactor overflowed into the quench vessel, a pH of 5.0 was established by activating the NaOH pump via the pH controller. Once sufficient batch mixture and NaOH were charged to result in >550 g/l total solids, the DI water or pure mother liquor pump was turned on. At this time, the quench vessel overflowed via the overflow leg and the semi-batch start-up was completed.

For continuous operation, the quench vessel was operated with pH control and overflow until the desired mass of material was collected. At reaction shut down, supra, the quench vessel remained on pH control until the entire mass was quenched. 30 minutes after completion of the mass quenching, the pumps and the pH controller were tuned off and the quench vessel was drained.

The compound of the formula

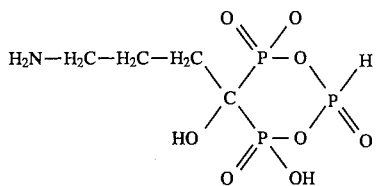

was produced and had the following characteristics:
a) Molecular weight=295; and
b) $^{31}P$ NMR at 161.98 MHz using $H_3PO_4$ (δ0.0) as an external reference standard δ3.8, (t, $J_{PP}$=13.5, $J_{PH}$=669.4) and δ15.9, (d, $J_{PP}$=13.5); and
c) $^{13}C$ NMR at 100.61 MHz using dioxane (δ67.4) as an external reference standard δ83.2, (td, $J_{CP}$=134.9, 10.4), δ41.2, δ31.8 (d, $J_{CP}$=3.2), δ23.8 (t, $J_{CP}$=6.4).

The compound of the formula

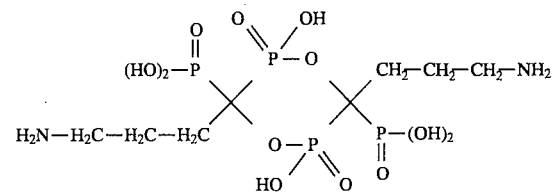

was also produced and had the following characteristics
a) Molecular weight=462; and
b) $^{31}P$ NMR at 161.98 MHz using $H_3PO_4$(δ0.0) as an external reference standard δ12.9 (t, $J_{PP}$=17.1), 8.0 (t, $J_{PP}$=17.1); and
c) $^{13}C$ NMR at 100.61 MHz using dioxane (δ67.4) as an external standard δ86.4 (ddd, $J_{CP}$=139.7,129.3,15.3), δ41.0, δ33.3, δ23.0(m).

Hydrolysis was carried out in a 250 ml Ace glass heavy walled safety coated storage bottle equipped with a Teflon™ coated magnetic stir bar and a modified Teflon™ cap to include a Teflon™ coated thermocouple that allowed in situ temperature monitoring. The vessel was suspended in a heated Silicon™ oil bath. 200 ml of quench material was charged to the hydrolysis vessel. The pH of the quench material was measured and adjusted accordingly to insure that the pH was between 4.6–5.5. The contents of the hydrolysis vessel were heated to 140° C. Once the proper temperature was reached the hydrolysis was aged for 20 hours at 140° C. After the aging was completed, the contents of the vessel were allowed to cool to 85° C. and the pH was checked and adjusted to 4.3 by addition of 50% NaOH or 37% HCl.

Crude crystallization was carried out in a 3-neck 250 ml round bottom flask equipped with a teflon paddle. 200 ml of 85° C. solution from the hydrolysis vessel were charged to the 250 ml 3-neck round bottom flask with stirring. The pH of the solution was measured and adjusted accordingly. However, if the pH was below 4.0, the solution was discarded and a new hydrolysis was done. The solution was allowed to cool to 20°–25° C. during which time the batch crystallized. The slurry was aged for >15 hours at room temperature with stirring and filtered with vacuum. The crystals were washed with 2×15 ml 0°–5° C. DI water. The product was dried overnight in vacuo at 45°–50° C.

The purification was carried out in a 3-neck 250 ml round bottom flask equipped with a teflon paddle. 10 g of dry crude material was charged into the 3-neck flask. 150 ml of DI water was charged to the flask. The flask was heated to 50° C. and held at that temperature until all the solids were dissolved. The flask was removed from the heat and the contents were filtered by vacuum. The filtrate was charged to the 3-neck flask and atmospherically distilled to 44 ml. The flask was removed from the heat and allowed to cool to room temperature. The contents of the flask were allowed to age for two hours. The slurry was cooled to 0°–5° C., aged for two hours and filtered with vacuum. The crystals were washed with 2×15 ml 0°–5° C. water.

EXAMPLE 2

Continuous preparation of (a) 2-amino-1-hydroxyisobutylidene-1,1-bisphosphonic acid, (b) 3-amino-1-hydroxypropylidene-1,1-bisphosphonic acid, (c) 5-amino-1-hydroxypentylidene-1,1-bisphosphonic acid or (d) 6-amino-1-hydroxyhexylidene-1,1-bisphosphonic acid Using the appropriate aminocarboxylic acid in equivalent amounts to 4-aminobutyric acid it is possible to produce the title bisphosphonic acids using the method of Example 1. The appropriate aminocarboxylic acid include but are not limited to: 2-aminoisobutyric acid, 3-aminopropionic acid, 5-aminovaleric acid and 6-aminocaproic acid.

EXAMPLE 3

Continuous preparation of (a)risedronate, and (b) BM210955

Using the appropriate starting materials, it is possible to produce the title compounds using the method of Example 1. Starting materials include: but are not limited to: 3-pyridylacetic acid, and N-butyl-N-methyl-3-amino propionic acid.

What is claimed is:

1. A compound of the structural Formula I $Z$—$R_1$

I wherein Z is selected from the group consisting of:

a) $H_2N$—$C_{2-5}$alkyl—;

$R_1$ is:

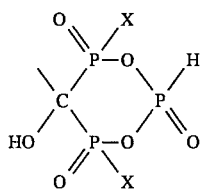

a)

wherein X is —OH or Cl.

2. A compound according to claim 1, having the formula $H_2N$—$C_{2-5}$alkyl—$R_1$ wherein $R_1$ is:

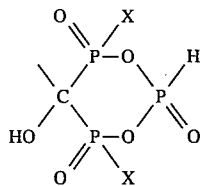

a)

wherein X is OH or Cl.

3. The compound of claim 2 of the formula $H_2N$—$CH_2$—$CH_2$—$CH_2$—$R_1$.

4. The compound of claim 3 wherein $R_1$ is

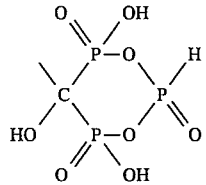

and is characterized by a) Molecular weight=295; and b) $^{31}P$ NMR at 161.98 MHz using $H_3PO_4$ (δ0.0) as an external reference standard δ3.8, (t, $J_{PP}$=13.5, $J_{PH}$=669.4) and δ15.9, (d, $J_{PP}$=13.5); and c) $^{13}C$ NMR at 100.61 MHz using dioxane (δ67.4) as an external reference standard δ83.2, (td, $J_{CP}$=134.9, 10.4), δ41.2, δ31.8 (d, $J_{CP}$=3.2), δ23.8 (t, $J_{CP}$=6.4).

5. A compound according to claim 1 having the formula $C_{2-6}$alkyl—(N—$CH_3$)$C_2H_4$13 $R_1$.

* * * * *